United States Patent [19]

Thomas, III

[11] Patent Number: 4,758,803

[45] Date of Patent: Jul. 19, 1988

[54] MARGINAL OSCILLATOR FOR ACOUSTIC MONITORING OF CURING OF PLASTICS

[75] Inventor: Lewis J. Thomas, III, Schenectady, N.Y.

[73] Assignee: General Electric Company, Schenectady, N.Y.

[21] Appl. No.: 73,250

[22] Filed: Jul. 13, 1987

[51] Int. Cl.⁴ .......................... B29G 7/00; H03B 5/00
[52] U.S. Cl. ........................................ 331/65; 264/23; 264/40.1; 425/174.2; 324/71.1; 331/154; 331/183
[58] Field of Search .......................... 331/65, 154, 183; 264/40.2, 23, 40.1; 425/174.2; 324/71.1

[56] References Cited

U.S. PATENT DOCUMENTS 3,791,792 2/1974 Lindsay ....................... 264/40.2 X
4,455,268 6/1984 Hinrichs et al. ............. 264/40.2 X

OTHER PUBLICATIONS

W. P. Winfree, F. R. Parker, "Measurement of the Degree of Cure in Epoxies With Ultrasonic Velocity", Rev. of Progress in Quant. NDE, 1985, vol. 5B, Plenum Press.
D. R. Dietz, "Ultrasonic Detection of Microemboli: Physical Principles and Physiological Results", Ph.D.Thesis, Washington Univ., 1976, pp. ii, iii, 35–92, 147–151, 157–159.
M. S. Conradi, J. G. Miller, J. S. Heyman, "A Transmission Oscillator Ultrasonic Spectrometer", Rev. Sci. Instrum., 45, 358–360, Mar., 1974.

Primary Examiner—Siegfried H. Grimm
Attorney, Agent, or Firm—Donald R. Campbell; James C. Davis, Jr.; Paul R. Webb, II

[57] ABSTRACT

Changes in the ultrasonic properties of fiber-reinforced plastics during the curing process are monitored by a marginal oscillator to determine the degree of cure. The plastic sample and transmitting and receiving transducers serve as a narrowband acoustic resonator and are placed in the feedback loop of a variable gain amplifier; using gain control the system is allowed to marginally oscillate. The resonant frequency of the sample and amplifier gain are related to the velocity and attenuation of sound in the plastic and are determined by measuring the received signal frequency and amplifier gain control voltage. The system has frequency locking means to track changes in resonant frequency during the cure cycle.

10 Claims, 3 Drawing Sheets

MARGINAL OSCILLATOR FOR ACOUSTIC MONITORING OF CURING OF PLASTICS

BACKGROUND OF THE INVENTION

This invention relates to a system to monitor changes in acoustic properties during the curing of plastics, and more particularly to a narrowband acoustic technique to make the measurements and the use of a marginal oscillator.

Present technology for curing of fiber-reinforced plastics uses a curing cycle which is empirically determined for the material of interest. Utilization of "smart press" technology to adjust the parameters of the cure, such as temperature and pressure, in response to the state of the material during the cure requires a non-invasive technique for evaluating the degree of cure of the plastic while the cure is in progress. During a cure, plastics undergo large changes in elastic moduli. Therefore, changes in ultrasonic properties such as velocity and attenuation should provide a sensitive and reliable measure of the degree of cure. What is needed is an improved means for determining the velocity and attenuation of ultrasound of a fiber-reinforced plastic during curing which is accurate and yet easy to apply in production work.

As the resin of a fiber-reinforced plastic cures, bonds form between the various polymer chains, and this increasingly complex linkage results in progressive increases in the viscosity, bulk modulus, and shear modulus of the resin matrix and of the overall composite. Longitudinal ultrasonic velocity data demonstrating these changes in epoxy carbon composites have been taken by W. P. Winfree and F. R. Parker, "Measurement of the Degree of Cure in Epoxies with Ultrasonic Velocity", Rev. of Progress in Quantitative NDE, 1985, Vol. 5B, Plenum Press. Previous measurements of velocity have been made using short, broadband pulses. Although this technique is conceptually straightforward, difficulties (due to the highly frequency-dependent attenuation of the composite) in producing pulses which are short enough to allow temporal resolution of distinct echoes from the sample has limited the efficacy of these pulse-echo techniques.

One reference where a marginal oscillator is discussed, in a medical application to measure changes in ultrasonic attenuation due to scattering and absorption of particles in a fluid, is the Ph.D. Thesis of Dennis R. Dietz, Washington University, St. Louis, 1976. Another is M. S. Conradi, J. G. Miller and J. S. Heyman, Rev. Sci. Instrum., 45, 358–360, 1974.

SUMMARY OF THE INVENTION

An object of the invention is to provide a robust and accurate technique for determining changes in ultrasonic velocity and attenuation of plastics during curing.

Another object is an improved system for making these measurements using a marginal oscillator and the sample as a narrowband acoustic resonator.

Marginal oscillators provide a simple and yet highly accurate technique for monitoring changes in the acoustic properties of fiber-reinforced and other plastics during the cure cycle. Such a system for determining both the attenuation and velocity of sound in the sample has the following components. A variable gain amplifier is provided whose gain is adjusted by a gain control signal, and the acoustic resonator is placed in a positive feedback loop of the amplifier. An amplitude control feedback loop has means to detect the amplifier output signal and adjust the gain control signal, and therefore amplifier gain, such that the output signal is substantially constant. The acoustic resonator is comprised of a mold containing the sample of plastic, whose resonant frequency and attenuation change as the sample is cured, and transmitting and receiving transducers on the mold to generate ultrasonic waves that pass through the sample and are received. Means are provided to measure the resonant frequency and amplifier gain which are respectively related to the velocity of sound and attenuation in the sample. Preferably the received signal frequency and gain control voltage are measured to determine the degree of cure.

Another feature of the invention is that the marginal oscillator system may have frequency locking means, such as a phase-locked loop, for tracking the resonant frequency as it increases during the cure cycle.

DETAILED DESCRIPTION OF THE INVENTION

Figure 1:
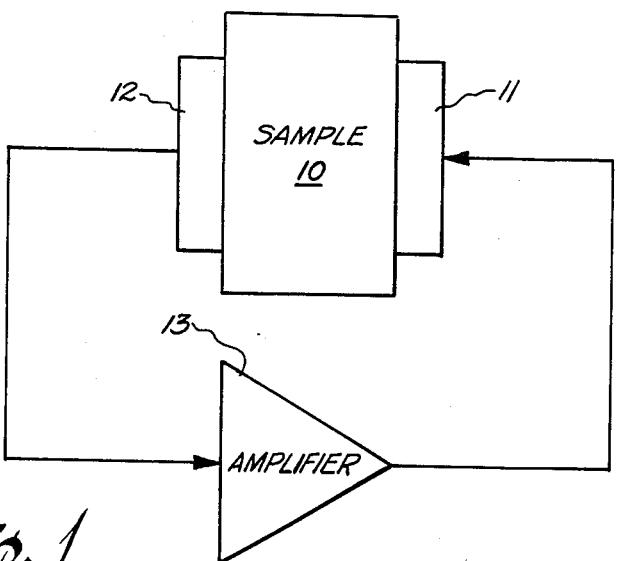
FIG. 1 shows a marginal oscillator for measuring the resonant frequency, and therefore the velocity of sound, of a sample of fiber-reinforced plastic.

Referring to FIG. 1, in its simplest form a marginal oscillator is comprised of a resonant sample 10, a transmitting ultrasonic transducer 11 and receiving ultrasonic transducer 12, and a variable gain amplifier 13 which feeds the received signal back to the transmitting transducer. The two transducers 11 and 12 and the sample 10 serve as a narrowband acoustic resonator and may be considered a feedback loop for the amplifier 13. Transmitting transducer 11 generates acoustic waves that are received by the receiving transducer 12 and at certain frequencies, resonant frequencies of the sample 10, there is a standing wave pattern. At every other resonant frequency signals will have a zero phase shift across the feedback loop (at the other resonant frequencies the phase shift is $\pi$ radians), therefore at these zero phase shift frequencies the loop represents a positive feedback path. If the gain of the amplifier is greater than the attenuation of the sample, then the signals of appropriate frequency will increase in amplitude until some non-linear response of the amplifier, usually clipping at the power supply levels, reduces the gain of the amplifier. The resonant frequency of the sample is determined by measuring the frequency of the received signal.

Figure 2:
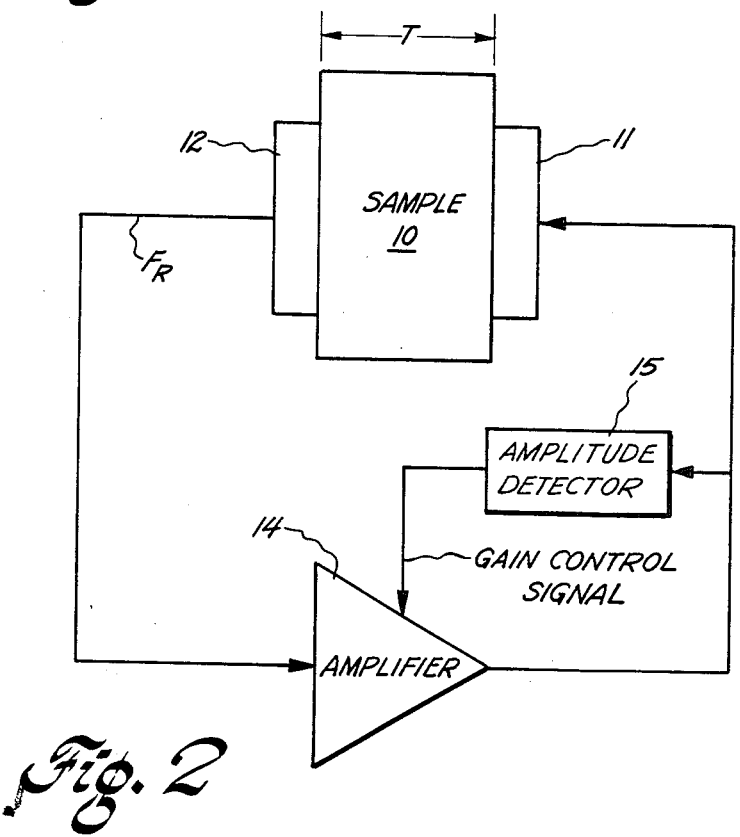
FIG. 2 shows a marginal oscillator system which determines the attenuation of the sample as well as the resonant frequency.

In order to determine the attenuation of a sample using a marginal oscillator, it is only necessary to modify the system shown in FIG. 1 slightly. In FIG. 2, a marginal oscillator system is presented to which there is added an amplitude control feedback loop. The amplifier is a variable gain or automatic gain control (AGC)

amplifier 14 for which the gain can be controlled by an external voltage. An amplitude detector 15, which may be as simple as a series diode and a capacitor to ground, is used to adjust the gain of variable gain amplifier 14 such that the amplitude of the output signal from the amplifier is constant. In order for this condition to occur, the gain of variable gain amplifier 14 must be equal to the attenuation of the sample 10. As the attenuation of the sample changes, a compensating change in the gain of variable gain amplifier 14 will occur. Therefore, the attenuation of the sample is monitored simply by sensing and measuring the gain of amplifier 14, which is usually done by measuring the voltage level of the gain control signal.

For many applications, the marginal oscillator system shown in FIG. 2 is sufficient for monitoring the changes in the velocity of sound in a sample, through changes in the resonant frequency, and attenuation of a sample. The velocity of sound, $V_s$, and zero phase shift resonant frequency, $f_R$, are related as given in the equation $$f_R = n \frac{V_s}{T},$$

where T is the separation between transducers (FIG. 2) and n is the harmonic and is an integer. If the resonant frequency at two harmonics n and n+1 are known, the difference in resonant frequencies is multiplied by T to give the velocity of sound. The resonant frequency is equal to the received signal frequency and is easily measured by a frequency counter at this point. The amplifier gain is controlled such that it is equal to the attenuation of the sample; the gain control voltage is measured to determine attenuation. When the sample is a plastic whose velocity and attenuation change during the cure cycle, these acoustic properties may be monitored to provide an indication of the degree of cure.

Figure 3:
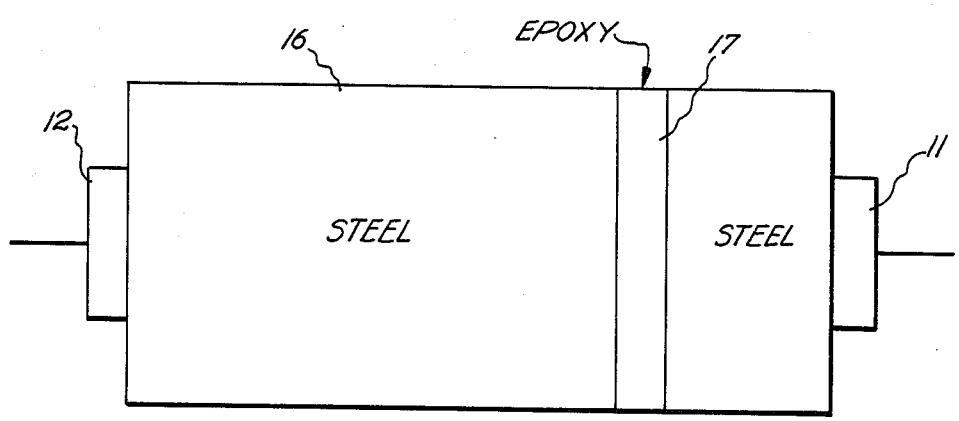
FIG. 3 illustrates an ultrasonic resonator used in experiments.
Figure 4:
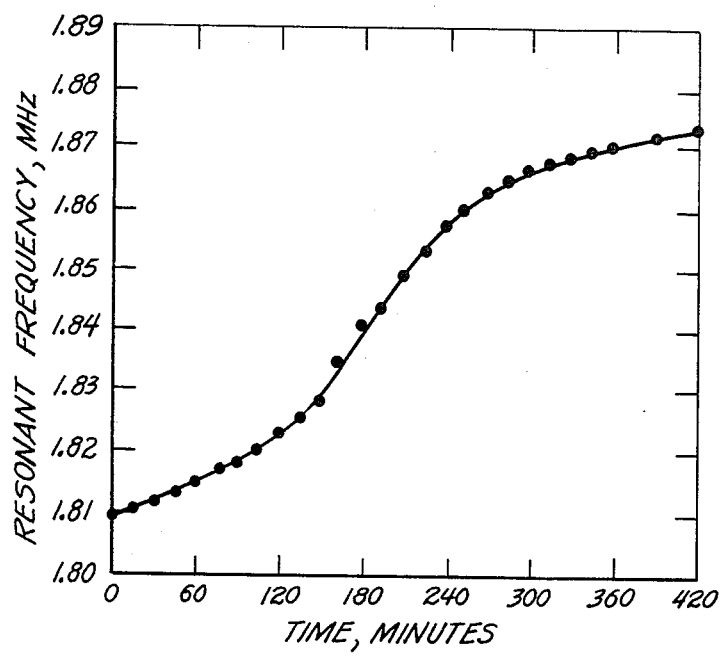
FIG. 4 shows the change in resonant frequency of the epoxy sample during the cure cycle.

Experimental data was taken during the curing of a fiber-reinforced epoxy using the narrowband acoustic resonator illustrated in FIG. 3. A steel mold 16 has a cavity 17 containing the sample of epoxy, and the transmitting and receiving transducers 11 and 12 are mounted on the parallel end faces of the mold. The transducers are broadband lead niobate 2 MHz devices. FIG. 4 shows the variation of resonant frequency with cure time, from 1.81 MHz at the start to about 1.88 MHz at the end. The change in attenuation is not shown, but generally follows the derivative; it has a low value at the start (a few dB/cm), increases to a peak where the change in resonant frequency is the steepest, and comes back down to a low value.

The application of interest is monitoring the curing of a fiber-reinforced plastic, for instance, graphite reinforced PMR-15, graphite reinforced epoxy, and glass reinforced epoxies and polyesters. For this application, a problem to be overcome results from the fact that the resonant frequency of the sample of plastic will be approximately 100 KHz, but it is desired to make the velocity measurements in the low MHz range. The motivation for working in the low MHz range is that a modest fractional bandwidth, say 10%, will easily span the range of frequency the resonance changes over during the cure cycle. Working in the low MHz range requires the use of a rather high (around 20) harmonic of the resonant frequency. It is relatively easy for the change in resonant frequency to exceed the spacing of consecutive resonances. In order to insure that only one harmonic of the resonant frequency is selected for the marginal oscillator to operate at, and that this harmonic is tracked over the cure cycle, a frequency locking system is used.

Figure 5:
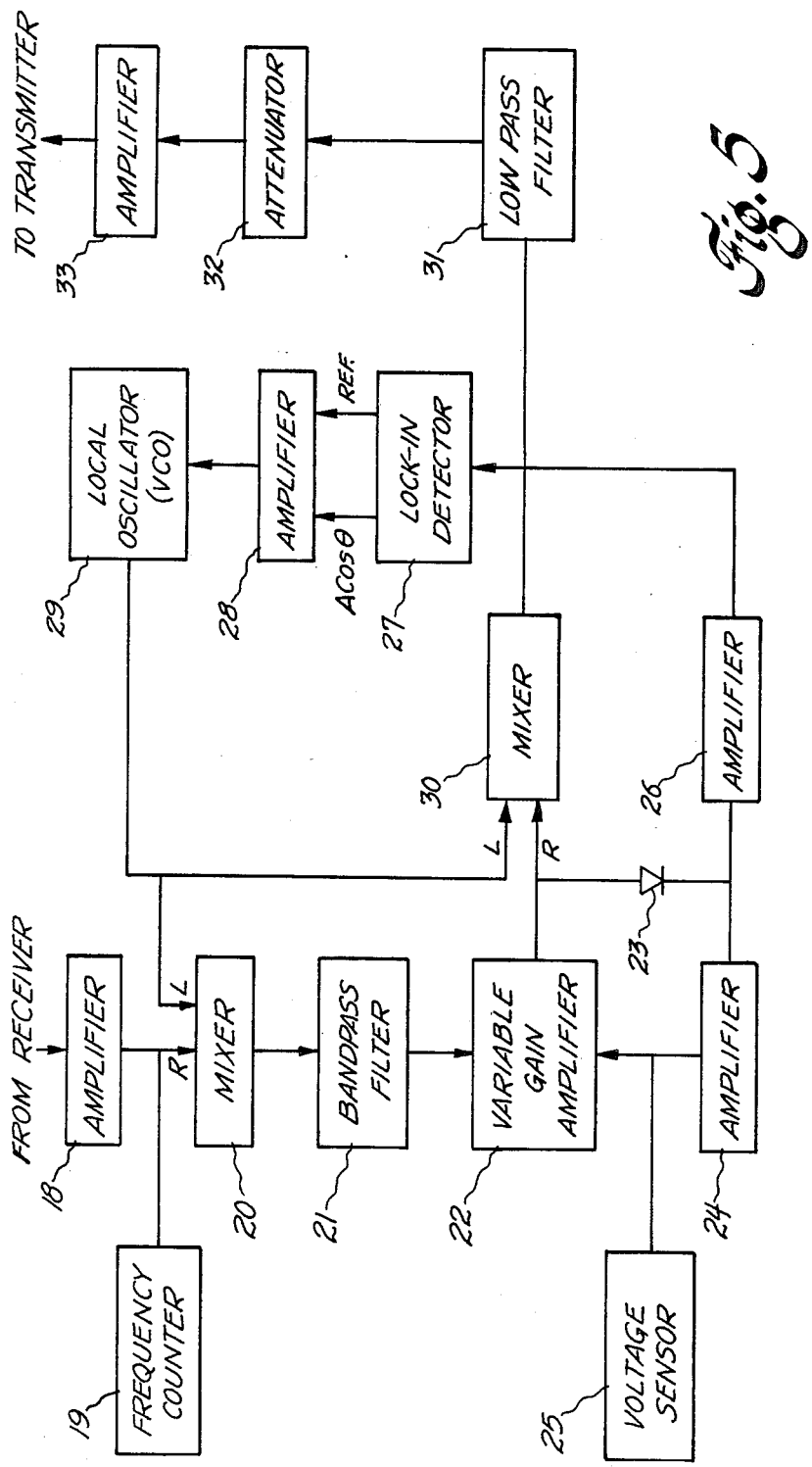
FIG. 5 is a block diagram of the complete marginal oscillator system, less the ultrasonic resonator, with a frequency locking section to allow tracking of the resonant frequency of the sample.

The complete marginal oscillator system, less acoustic resonator, is shown schematically in FIG. 5. A phase-locked loop (components 20, 21, 26–29 and gain control components 22 and 23 acting in a dual capacity) is employed to track the resonant frequency of the sample as it increases during the cure cycle. The scheme introduces a small frequency modulation into the signal, which results in an amplitude modulation after the signal has been passed through the bandpass filter 21. The resulting amplitude modulation is detected by the lock-in amplifier 27, the output of which is fed back to the frequency control of local oscillator 29. This local oscillator is used to mix the input signal (at 20) to an appropriate intermediate frequency for the bandpass filter 21.

The received signal from the receiving transducer is amplified at 18 and a frequency counter. 19 is placed at the amplifier output to measure the resonant frequency. The received signal is mixed down to an intermediate frequency at 20 using the signal from local oscillator 29. If, for instance, the received signal has a frequency of 2 MHz, the local oscillator signal is 2.5 MHz+10 kHz, and the bandpass filter 21 has a 0.5 MHz center frequency; the result of the mixing is the sum and difference of the two input frequencies, both with a small modulating frequency. Bandpass filter 21 passes the intermediate frequency (0.5 MHz) but attenuates the higher frequency (4.5 MHz). The amplitude control feedback loop comprised of variable gain amplifier 22, diode detector 23, and amplifier 24, is placed after bandpass filter 21 in order to maintain a stable amplitude for the frequency locking loop. It also serves its main function of gain control to correct for any changes in the attenuation of the sample. Voltage sensor 25 measures the gain control voltage in order to determine attenuation.

The amplitude detected signal provided by diode 23 after passing through amplifier 26 is the input to lock-in detector 27. This device, which is also known as a phase sensitive amplifier, has two outputs, a reference signal (in the example a pure sine wave with a 10 kHz frequency) and an $A \cos\theta$ output representing the amplitude of the component of the detected input signal which is in phase with the reference signal. Consider the following three cases:

(1) The frequency of the IF is less than the center frequency of the bandpass filter (local oscillator frequency minus resonant frequency equals the intermediate frequency). In this case the signal input to lock-in detector 27 has some amplitude at the reference signal frequency and a phase arbitrarily called positive for this discussion. Therefore the lock-in detector outputs a positive voltage which is fed to amplifier 28 and local oscillator 29 to increase its frequency and therefore the frequency of the IF. If the resonant frequency increases, the local oscillator frequency changes to keep the IF at the center of the bandpass filter.

(2) The frequency of the IF is equal to the center frequency of the bandpass filter. In this case the signal input to lock-in detector 27 has no amplitude at the reference frequency. Therefore lock-in detector 27 has no voltage at its other output, leaving the IF unchanged.

(3) The frequency of the IF is greater than the center frequency of bandpass filter 21. In this case the signal input to lock-in detector 27 has some amplitude at the reference frequency but with a negative phase (the opposite phase of case (1) since the operating point is on the other side of the bandpass). Therefore lock-in detector 27 has a negative output voltage which is fed back to local oscillator 29 through amplifier 28 to decrease the frequency of the local oscillator signal and therefore the IF.

As a final step in the frequency tracking system, the IF output of variable gain amplifier 22 is mixed back up to the original received frequency, the resonant frequency, and filtered to suppress harmonics from the mixing. The local oscillator signal and the gain controlled IF signal are presented to mixer 30. If the frequencies are 2.5 MHz and 0.5 MHz, the sum and difference are produced and a low pass filter 31 discriminates against the higher frequencies. The 2.0 MHz signal is presented to attenuator 32 and a power amplifier 33 to provide a driving voltage for the transmitting transducer.

The amplitude control feedback loop (components 22–24) is placed after bandpass filter 21 because the power levels required for stable operation are too high if it is put before mixer 20. The feedback signal for the frequency locking system is derived from the amplitude detected output of bandpass filter 21. The phase of the detected signal changes as the IF sweeps past the center frequency of the bandpass filter, and the amplitude of the detected signal decreases. Putting the amplitude control feedback loop ahead of mixer 20 gives the result that the phase response of the frequency locking system is correct but it is degraded by an incorrect amplitude response. The solution is to position the amplitude control feedback loop after bandpass filter 21, thereby maintaining a stable amplitude for the phase-locked loop.

In conclusion, utilization of a marginal oscillator and a narrowband resonant technique to monitor the curing of plastics and measure changes in both velocity of sound and attenuation, results in a measurement system which is accurate, stable, and may be produced at reasonable cost.

While the invention has been particularly shown and described with reference to preferred embodiments thereof, it will be understood by those skilled in the art that the foregoing and other changes in form and details may be made without departing from the spirit and scope of the invention.

The invention claimed is:

1. A marginal oscillator for acoustic monitoring of the curing of a fiber-reinforced plastic comprising:
    a mold containing a sample of said plastic whose resonant frequency and attenuation change during curing and are indicative of the degree of cure;
    transmitting and receiving transducers on said mold to generate and receive ultrasonic waves that pass through said plastic;
    a variable gain amplifier whose gain is adjusted by a gain control signal and which has a positive feedback loop comprised of said mold with its sample and said transducers;
    an amplitude control feedback loop having means to detect the amplitude of the amplifier output signal and to produce said gain control signal to adjust amplifier gain such that said output signal is substantially constant; and
    means for measuring said resonant frequency and amplifier gain which are respectively related to the velocity and attenuation of sound in said fiber-reinforced plastic.

2. The marginal oscillator of claim 1 wherein said last-mentioned means measures the received signal from said receiving transducer and said gain control signal.

3. The marginal oscillator of claim 1 further comprising frequency locking means for tracking the resonant frequency of said sample as it changes during the cure cycle.

4. The marginal oscillator of claim 3 wherein said frequency locking means is comprised of a phase-locked loop.

5. A system to monitor changes in ultrasonic properties of a fiber-reinforced plastic during a curing process comprising:
    a marginal oscillator comprised of a variable gain amplifier whose gain is adjusted by a gain control signal, an acoustic resonator serving as a positive feedback loop for said amplifier, and an amplitude control feedback loop having means to detect the amplifier output signal and adjust said gain control signal and amplifier gain such that said output signal is substantially constant;
    said acoustic resonator including a sample of said plastic whose resonant frequency and attenuation change during curing, and a transmitting transducer to generate ultrasonic waves that pass through said plastic to a receiving transducer; and
    means for measuring said resonant frequency and amplifier gain which are respectively related to the velocity and attenuation of sound in said sample.

6. The system of claim 5 wherein said last-mentioned means measures the received signal frequency from said receiving transducer and the voltage level of said gain control signal.

7. The system of claim 5 wherein said marginal oscillator has phase-locked loop means for tracking the resonant frequency of said sample as it increases during the cure cycle.

8. The system of claim 7 wherein said phased-locked loop means is comprised of means for mixing the received signal from said receiving transducer with a local oscillator signal that has a small modulation frequency, down to an intermediate frequency signal that is passed by a bandpass filter to said variable gain amplifier, and means for detecting the amplitude of the amplifier output and controlling a lock-in detector and in turn the frequency of said local oscillator signal.

9. The system of claim 8 further comprising means for mixing the amplifier output with said local oscillator signal and back up to the received signal frequency and low pass filtering to provide a driving signal for said transmitting transducer.

10. The system of claim 5 wherein said transmitting and receiving transducers are low megahertz transducers, and said marginal oscillator further comprises frequency locking means for tracking a given harmonic of the resonant frequency as it increases during the cure cycle.

* * * * *